DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JUNE 1, 1971

827 O.G. 6

T887,010
INHIBITING POLYMERIZATION OF VINYL MONOMERS

Arthur P. Werts III, 1362 Lafayette Circle, Kingsport, Tenn. 37664

Filed July 2, 1970, Ser. No. 52,080
Int. Cl. B01j *1/16;* C07c *17/42*
U.S. Cl. 252—404
No Drawing. 10 Pages Specification

Undesired polymerization of vinyl monomers, either in storage or while undergoing purification by distillation of the monomeric material (as a step in the process by which the monomers are synthesized), can be prevented by adding to the liquid monomer as a polymerization inhibitor small amounts of an alkyl ether of 2,6-di-tert-butyl hydroquinone such as 2,6-di-tert-butyl-4-octyloxyphenol; 2,6-di-tert-butyl-4-methoxyphenol; 2,2′-bis(3,5-di-tert-butyl-4-hydroxyphenoxy) - p - xylene; 1,4-bis(3,5-di-tert-butyl-4-hydroxyphenoxy)butane; 2,6-di-tert-butyl-4-benzoyloxyphenol; and 1,4-bis(3,5-di-tert-butyl - 4 - hydroxyphenoxy)-p-xylene. By employing an inhibitor of this type, undesired polymerization of the monomer in storage, purification, or use is effectively prevented. This class of inhibitors contribute no undesirable color to vinyl monomers to which they are added and do not interfere in any way with subsequent processing of the stabilized monomer into any desired ultimate product.